(12) United States Patent
Thomas et al.

(10) Patent No.: US 12,121,287 B2
(45) Date of Patent: Oct. 22, 2024

(54) DRIVE SHAFT FOR A SURGICAL INSTRUMENT

(71) Applicant: GYRUS MEDICAL LIMITED, Cardiff (GB)

(72) Inventors: Daniel Thomas, St Mellons (GB); Marno Nagtegaal, St Mellons (GB); Nafiseh Ahanchian, St Mellons (GB)

(73) Assignee: GYRUS ACMI, INC, Bartlett, TN (US)

( * ) Notice: Subject to any disclaimer, the term of this patent is extended or adjusted under 35 U.S.C. 154(b) by 292 days.

(21) Appl. No.: 17/240,668

(22) Filed: Apr. 26, 2021

(65) Prior Publication Data
US 2021/0330376 A1 Oct. 28, 2021

(30) Foreign Application Priority Data
Apr. 24, 2020 (GB) ..................................... 2006039

(51) Int. Cl.
*A61B 18/14* (2006.01)
*A61B 17/29* (2006.01)
*A61B 18/00* (2006.01)

(52) U.S. Cl.
CPC .. *A61B 18/1447* (2013.01); *A61B 2017/2938* (2013.01); *A61B 2018/00589* (2013.01)

(58) Field of Classification Search
CPC ...................... A61B 18/1447; A61B 2017/2938
See application file for complete search history.

(56) References Cited

U.S. PATENT DOCUMENTS

| | | | |
|---|---|---|---|
| 2012/0065466 A1* | 3/2012 | Slater ................... | A61B 17/295 600/104 |
| 2012/0172924 A1 | 7/2012 | Allen, IV | |
| 2013/0023868 A1* | 1/2013 | Worrell ............ | A61B 17/07207 606/205 |
| 2013/0282031 A1 | 10/2013 | Woodard, Jr. et al. | |
| 2014/0379014 A1 | 12/2014 | Abri et al. | |
| 2019/0008536 A1* | 1/2019 | Forster ............... | A61B 17/3201 |

OTHER PUBLICATIONS

Oct. 14, 2020 Search Report issued in Great Britain Application No. GB2006039.8.
Feb. 8, 2022 Office Action issued in Japanese Patent Application No. 2021-073310.
Mar. 28, 2024 Office Action issued in European Patent Application No. GB2006039.8.

* cited by examiner

*Primary Examiner* — Linda C Dvorak
*Assistant Examiner* — Ryan T Clark
(74) *Attorney, Agent, or Firm* — Oliff PLC

(57) ABSTRACT

An improved drive shaft for controlling an end effector of surgical instrument having advantages over the prior art, specifically, the drive shaft includes two separate elongate elements, each including a flange at its proximal end for restricting the lateral movement of the drive shaft when installed within an outer shaft of the instrument. The dimensions of the flanges are such that they fit within the outer shaft with minimal clearance. This allows the drive shaft to be moved longitudinally within the outer shaft to actuate an end effector whilst minimizing any lateral movement. This consequently prevents the end effector from tilting as it is actuated. The drive members are arranged so that the flanges extend in opposite directions perpendicular to the length of the drive shaft. This helps to improve ease of assembly and provides space within the outer shaft for features such as connection wires and the like.

14 Claims, 11 Drawing Sheets

DRIVE SHAFT FOR A SURGICAL INSTRUMENT

TECHNICAL FIELD

Embodiments of the present invention described herein relate to a drive shaft for a surgical instrument, and in particular a drive shaft for controlling an end effector of a surgical instrument.

BACKGROUND TO THE INVENTION

It is known to provide a surgical instrument with a pair of opposing jaw members disposed on the end of an elongate shaft and configured to grasp tissue therebetween. The jaw members are pivotally connected and moveable by means of a drive assembly comprising a drive shaft configured to move a drive pin along slots disposed on each of the jaw members such that one or both of the jaw members move relative to the other to thereby move between open and closed positions. A blade assembly is also often provided, with the blade assembly being moveable along a track within the drive shaft such that the blade assembly can be translated between the first and second jaw members to cut tissue grasped therebetween. The draft shaft therefore controls both the opening and the closing of the jaw members, whilst also maintaining a level of rotational control to prevent the jaw members from tilting during use, that is, to keep the jaws in line with the longitudinal axis of the drive shaft.

To prevent the jaw members from tilting in prior art devices, the drive shaft is provided with an elongate slot at the distal end of the shaft in front of the drive pin arrangement. This elongate slot is arranged to receive the pivot pin connecting the two jaw members, such that the elongate slot slides over the pivot pin as the drive shaft is translated back and forth, thereby providing a two-point constraint of the jaw members.

SUMMARY OF THE INVENTION

Embodiments of the present invention provide an improved drive shaft for controlling an end effector of surgical instrument having advantages over the prior art. Specifically, the drive shaft comprises two separate elongate elements, each comprising a flange at its proximal end for restricting the lateral movement of the drive shaft when installed within an outer shaft of the instrument. The dimensions of the flanges are such that they fit within the outer shaft with minimal clearance. This allows the drive shaft to be moved longitudinally within the outer shaft to actuate an end effector whilst minimising any lateral movement. This consequently prevents the end effector from tilting as it is actuated. The drive members are preferably arranged so that the flanges extend in opposite directions perpendicular to the length of the drive shaft. This helps to improve ease of assembly and provides space within the outer shaft for features such as connection wires and the like.

A first aspect of the present invention provides a drive shaft for a surgical instrument, comprising:
- a pair of opposing first and second elongate drive members, wherein a distal end of the first and second elongate drive members are configured to actuate an end effector of the surgical instrument; characterized in that:
- the first elongate drive member comprises at least a first flange extending from its distal end in a first direction perpendicular to the longitudinal axis of the drive shaft; and
- the second elongate drive member comprises at least a second flange extending from its distal end in a second direction perpendicular to the longitudinal axis of the drive shaft.

As such, the drive shaft is formed of two separate elements that lie in parallel with one another. The distal end of these separate elements each have a flange extending in a direction perpendicular to the longitudinal axis of the drive shaft. When installed within an outer shaft of a surgical instrument, these flanges abut against the inner walls of the outer shaft to prevent the drive shaft from moving laterally as it translates in a longitudinal direction to actuate the end effector of said instrument, for example, a pair of jaws for grasping tissue, which in turn prevents the end effector from tilting.

Preferably, the first and second directions may be opposing directions. That is to say, the first and second flange extend away from each other. As a result of this arrangement, a space is provided next to each flange (i.e. above or below the adjacent flange) for routing other components of the end effector such as electrical wires.

The first and second elongate drive members may be connected at a first position towards the proximal end of the drive shaft.

Prior to installation in the surgical instrument, the distal end of the first elongate drive member may be moveable in a lateral direction relative to the distal end of the second elongate drive member so as to enable installation in a component of the surgical instrument. That is to say, the drive members may be squeezed together so that the effective diameter of the two flanges is reduced. This enables the drive shaft to be threaded through narrow openings in various components of the surgical instrument, such as a retention molding used for anchoring the end effector to a handle.

The distal end of the first and second elongate drive members may be configured to receive a drive pin for actuating the end effector. For example, each flange may comprise a drive pin hole that are aligned with each other. Once the drive pin is in place, this will lock the elongate drive members in place and prevent them from moving laterally relative to one another.

The first and second flanges may be configured such that the distal end of the drive shaft has a spade-like configuration.

A further aspect of the present invention provides an end effector for a surgical instrument, comprising:
- a pair of opposing first and second jaw members, the first and second jaw members being pivotally connected, each of the jaw members comprising a jaw flange extending from its proximal end, each flange having an elongate slot; and
- a drive assembly configured to move the first jaw member relative to the second jaw member from a first open position to a second closed position, the drive assembly comprising:
- a drive pin configured to be received by the elongate slots of the first and second jaw members, the drive pin being moveable between proximal and distal ends of the elongate slots; and
- a drive shaft as described above, wherein the first and second elongate drive members are further configured to receive the drive pin at the distal end of the drive shaft, the drive shaft being configured to move in a first direction along its longitudinal axis so as to actuate the drive pin longitudinally towards a distal end of the elongate slots to thereby move the first jaw member to the first open position, and further configured to move in a second direction along its longitudinal axis so as to actuate the drive pin longitudinally towards a proximal.

As discussed above, the flanges of each elongate drive member are configured to prevent lateral movement of the drive shaft as it moves along the longitudinal axis, thereby prevent the jaw members from tilting as they move between the open and closed position. Further, the drive shaft terminates at the drive pin and does not comprise any additional length extending further into the jaw members. As such, the drive assembly reduces the amount of space occupied within the jaw assembly, thereby providing greater design freedom.

The end effector may further comprise an outer shaft extending from the first and second jaw members, wherein the drive assembly is located within the outer shaft. In such cases, the first and second flanges of the first and second drive members are configured such that lateral movement within the outer shaft is restricted. That is to say, the flanges of the first and second drive members abut against the outer shaft so as to prevent lateral movement. In this respect, a diameter of the distal end of the drive shaft may substantially match an internal diameter of the outer shaft. That is to say, the effective diameter of the flanges substantially corresponds to the inner diameter of the outer shaft.

The end effector may further comprise one or more electrical wires for connecting the first and second jaw members to a power supply, wherein the one or more electrical wires are arranged to run alongside one or both of the first and second elongate drive members such that the one or more electrical wires are positioned away from the first and/or second flange.

The end effector may further comprise a blade assembly, the blade assembly having a cutting blade located at its distal end, wherein the cutting blade assembly is arranged to be moved in a longitudinal direction between the first and second elongate drive members such that the cutting blade is translated between the first and second jaw members.

A further aspect of the present invention provides a surgical instrument, comprising an end effector as described above.

BRIEF DESCRIPTION OF THE DRAWINGS

Embodiments of the invention will now be further described by way of example only and with reference to the accompanying drawings, wherein like reference numerals refer to like parts, and wherein.

DETAILED DESCRIPTION OF THE EMBODIMENTS

Figure 1:
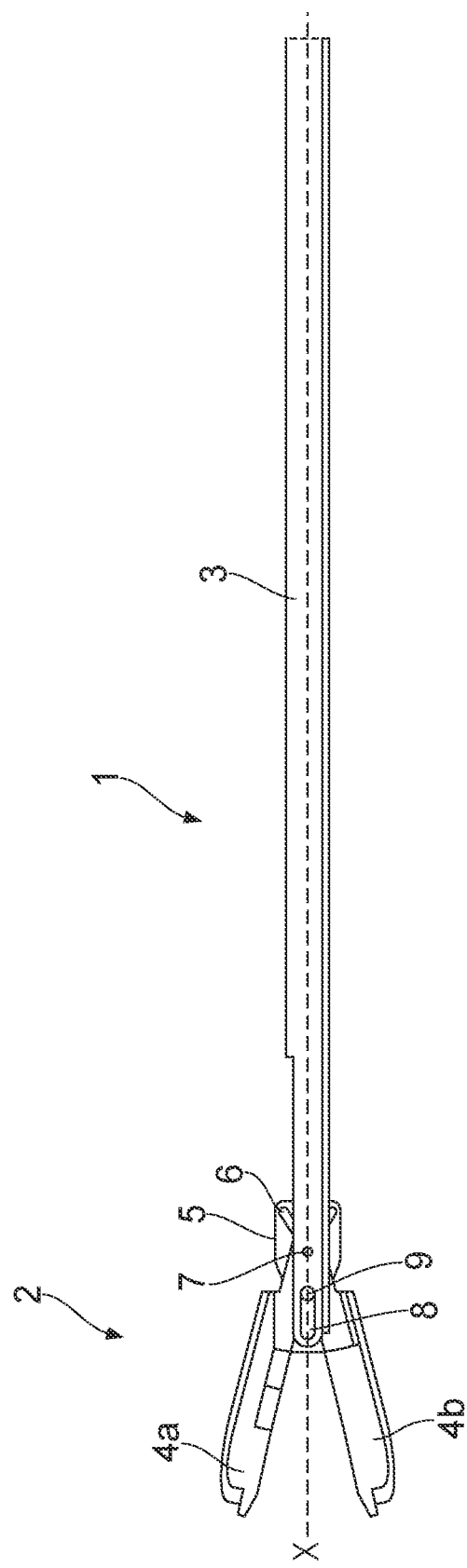
FIG. 1 illustrates a prior art drive assembly for an end effector.

As discussed above, tilt in the jaw members of prior art devices is prevented by providing the drive shaft with an elongate slot at the most distal end, as shown in FIG. 1.

In FIG. 1, a drive assembly 1 arranged to control a jaw assembly 2 is shown, the drive assembly comprising a drive shaft 3 arranged to drive a pair of opposing jaw members 4a, 4b. The jaw members 4a, 4b each comprise a flange 5 having a slot 6 through which a drive pin 7 extends. A proximal and distal movement of the drive pin 7 along the slots 6 by means of the drive shaft 3 causes one or both of the jaw members 4a, 4b to move relative to the other such that the jaw members 4a, 4b move between an open position and a second position. The drive shaft 3 may be actuated by any suitable mechanism, for example, a trigger located on a handle (not shown) at the proximal end of the instrument.

Beyond the drive pin 7, drive shaft 3 further comprises an elongate slot 8 that is arranged to receive the pivot pin 9 that pivotally connects the jaw members 4a, 4b. As the drive shaft 2 translates in a proximal and distal direction, the elongate slot 8 slides over the pivot pin 9 to thereby provide a two-point constraint of the jaw members 4a, 4b. This ensures that the jaw member 4a, 4b do not tilt relative to the longitudinal axis (denoted X) of the drive shaft 3, such that the jaw member 4a, 4b open symmetrically about the centre line of the longitudinal axis X. However, this requires an additional length of drive shaft 3 to be provided beyond the drive pin 7, which takes up more space within the jaw assembly 2.

The drive shaft 3 is typically a ⌐Ц⌐⌐ shape with a track (not shown) provided along its length for receiving a cutting blade assembly that translates therealong. In use, once the jaw members 4a, 4b are in the closed position so as to grasp a portion of tissue, the blade may be translated between the jaw members 4a, 4b so as to cut the tissue clasped therebetween.

As discussed above, the additional length of drive shaft 3 required for the elongate slot 8 uses up space inside the jaw member assembly 2, which can make manufacture challenging since the polymer mouldings have to be designed so that the jaws 4a, 4b sufficiently constrain the distal end of the cutting blade. In this respect, the cutting blade is very thin and sharp, and therefore needs to be constrained so that it can be aligned with the features that drive the blade into the jaw track during deployment, to thereby prevent it from bending and catching on other features.

Figure 2:
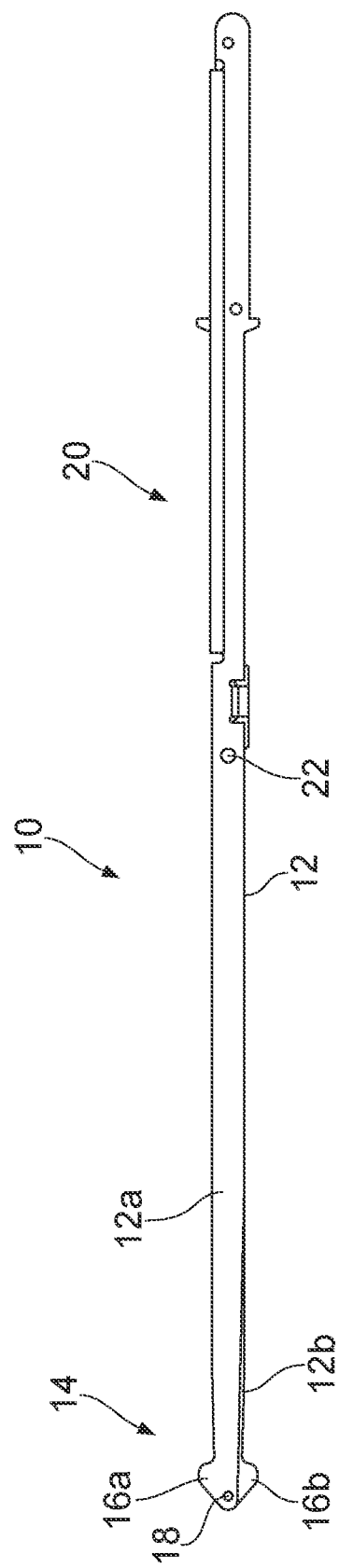
FIG. 2 illustrates a drive assembly according to the present invention.
Figure 3:
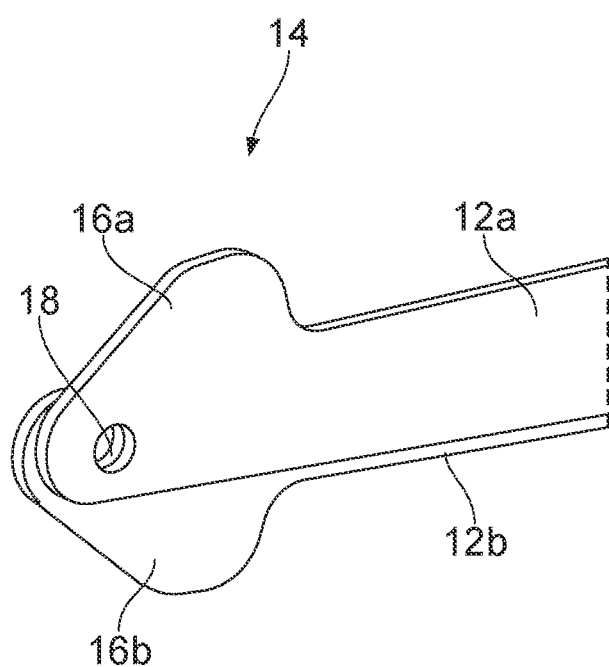
FIG. 3 shows part of the drive assembly of FIG. 2.

FIG. 2 illustrates a drive assembly 10 according to the present invention. The drive assembly 10 comprises a drive shaft 12 having two opposing elongate drive members 12a, 12b. The distal end 14 of the drive shaft 12 has a spade like configuration, wherein each drive member 12a, 12b comprises a flange 16a, 16b extending in opposite directions perpendicular to the longitudinal axis of the drive shaft 12, as shown further in FIG. 3. Each flange 16a, 16b comprises a drive hole 18 (only one shown) that aligns with the drive hole of the other flange. In use, this drive hole 18 will receive the drive pin of the jaw assembly in order to drive the jaw members. As such, there is no additional length of the drive shaft 12 beyond this drive hole 18 taking up unnecessary space inside the jaws.

The drive members 12a, 12b are coupled together towards the proximal end 20 of the drive assembly 10, for example, by means of a pin 22. By coupling the drive members 12a, 12b towards the proximal end 20, this allows for some lateral movement of the drive members 12a, 12b, which is important assembling the drive assembly 10 and the jaw assembly 2 together, as will be described in more detail below. The proximal end 20 of the drive assembly 10 can then be coupled to any suitable actuating mechanism for driving the drive shaft 12.

Figure 4A:
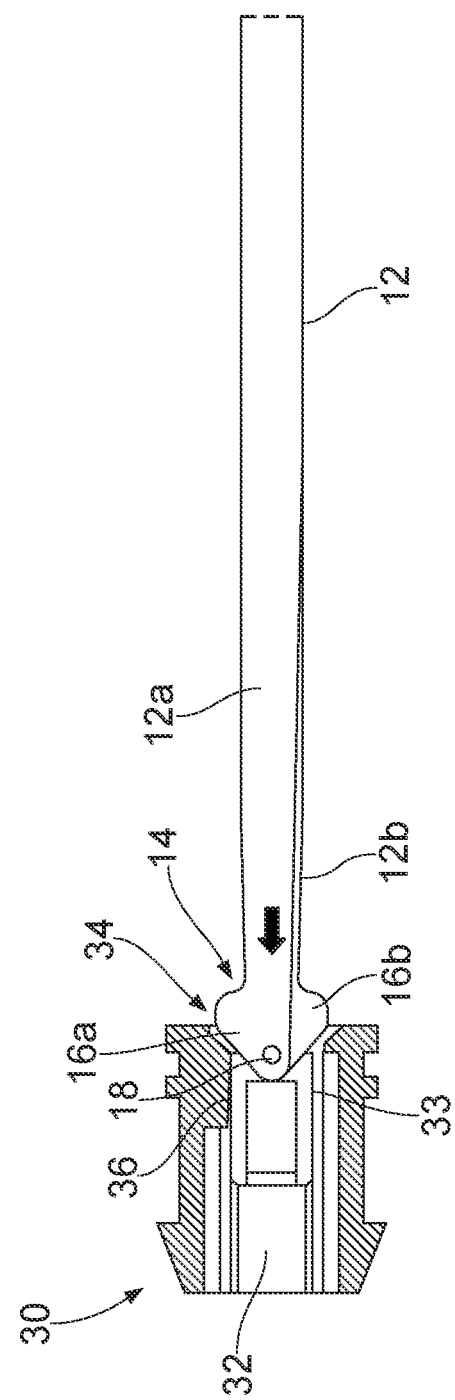
FIGS. 4A-4C illustrate a method of assembling the drive assembly of the present invention.
Figure 4B:
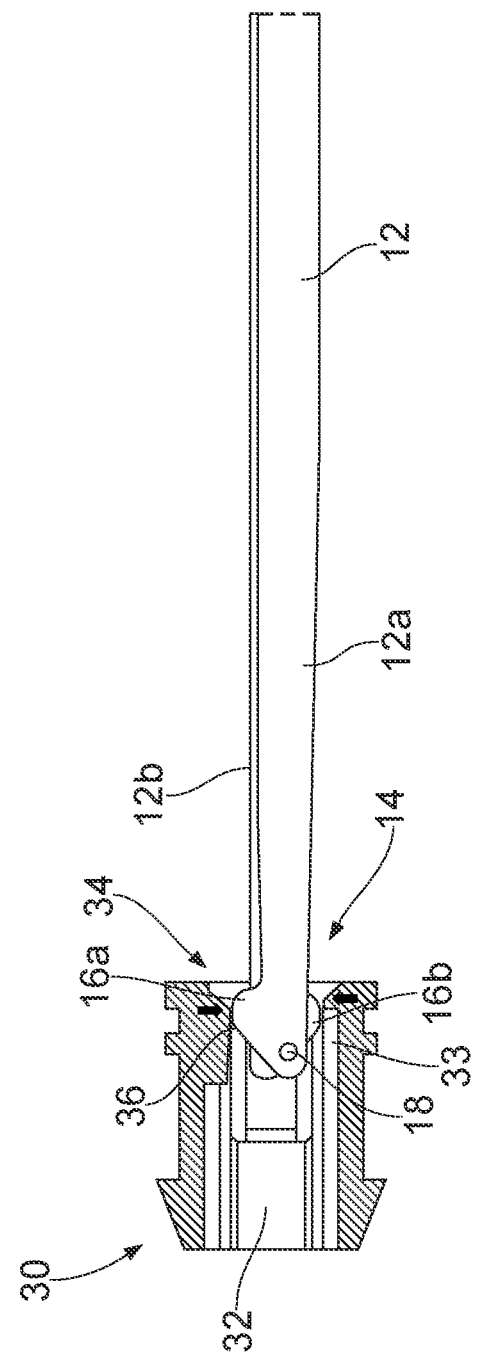
Figure 4C:
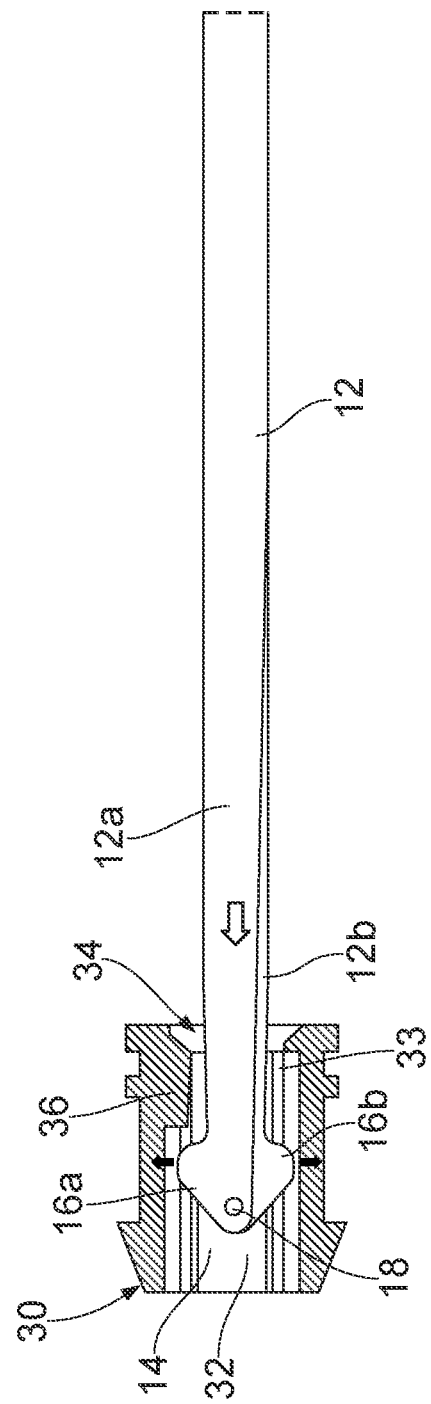
Figure 5:
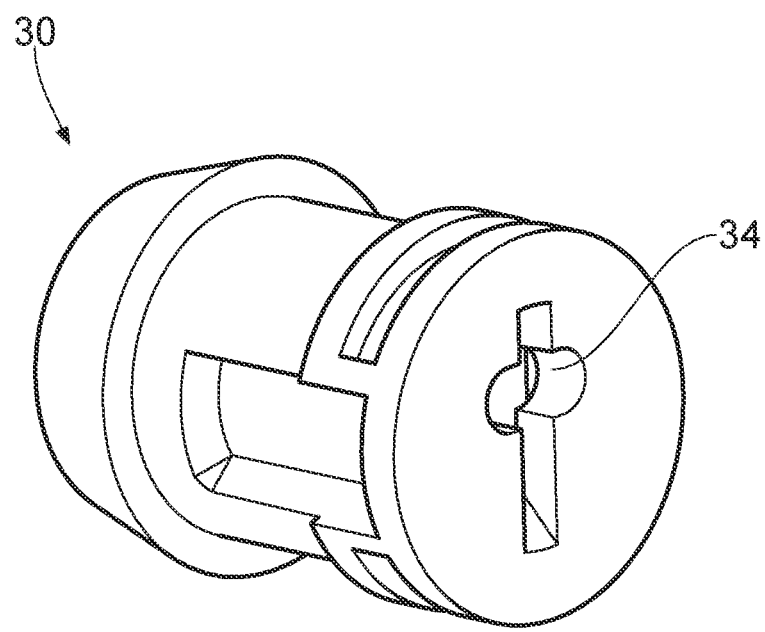
FIG. 5 illustrates a component for installing the drive assembly in a surgical instrument.

FIGS. 4A-4C illustrate a method of installing the drive shaft 12 within a shaft moulding 30 used for installing the drive assembly 1 in a surgical instrument. As shown in FIG. 5, the shaft moulding 30 is a barrel shaped component with an aperture 34 for receiving the drive shaft 12, which in this example has a ☐☐☐ shaped configuration, typically arranged in this way for receiving previous ⨆☐☐ shaped drive shafts.

To install the drive shaft 12, the distal end 14 of the drive shaft 12 is inserted to the aperture 34, as shown in FIG. 4A. At the proximal end, the shaft component 30 comprises an inner surface 36 so as to provide a narrow region 33 within the cavity 32 of the shaft component 30. The diameter of this narrow region 33 is smaller than the diameter of the distal end 14 of the drive shaft 12. As the drive shaft 12 is advanced into the shaft moulding 30, the inner surface 36 pushes against the flanges 16a, 16b such that the flanges 16a, 16b and the drive members 12a, 12b translate laterally towards each other. The flanges 16a, 16b may be squeezed together in this way by virtue of the pivotal connection 22 or by a degree of flexibility in the drive members 12a, 12b themselves. In doing so, the diameter of the distal end 14 is reduced to match that of the narrow region 33 within the shaft component 30, as shown in FIG. 4B, to thereby allow the drive shaft 12 to pass through. Once the drive shaft 12 moves beyond the narrow region 33, the flanges 16a, 16b are released and the drive members 12a, 12b move back to the starting position, as shown in FIG. 4C.

Figure 6:
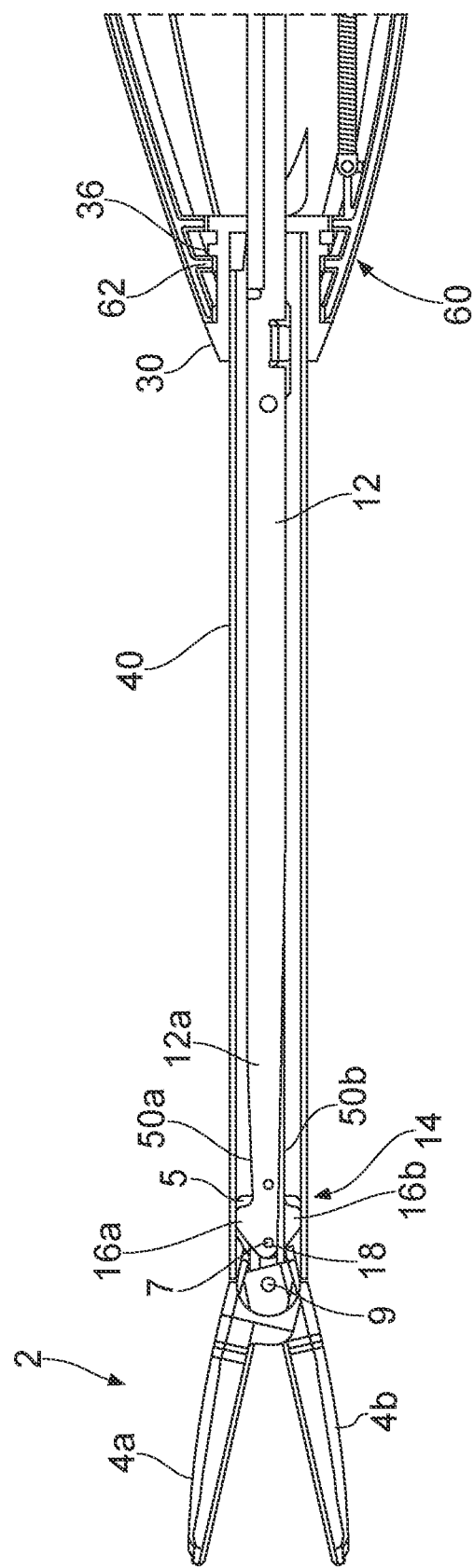
FIG. 6 illustrates the drive assembly of the present invention connected to an end effector.
Figure 8:
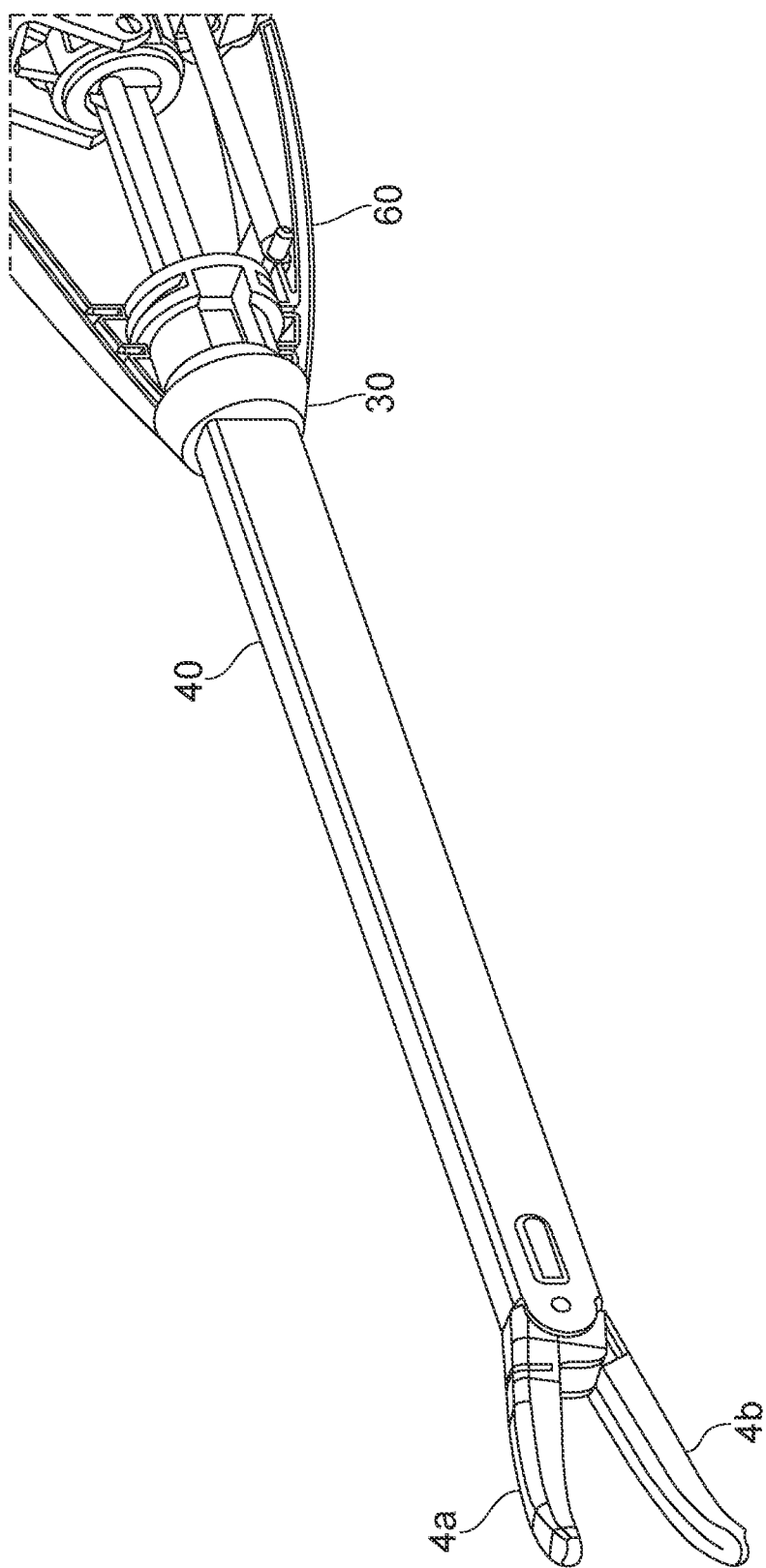
FIG. 8 illustrates an assembled end effect according to the present invention.

As illustrated by FIGS. 6 and 8, the shaft moulding 30 is then configured to sit within a socket of the casing 60 of the handle of the surgical instrument, and thus couples the drive shaft 12 to the casing 60. For example, the shaft moulding 30 may comprise a cylindrical flange portion 62 configured to cooperate with a corresponding concentric mating face 62 to thereby retain the shaft moulding 30 within the casing 60. The drive shaft is positioned such that the proximal end 20 sits within the casing 60, and the drive members 12a, 12b and the distal end 14 extend beyond the shaft component 30.

An outer shaft 40 may then be arranged around the outside of the drive shaft 12 and connected to the shaft moulding 30 by any suitable means, for example, a snap-fit arrangement or adhesive, thereby anchoring the whole end effector assembly to the casing 60.

Figure 7:
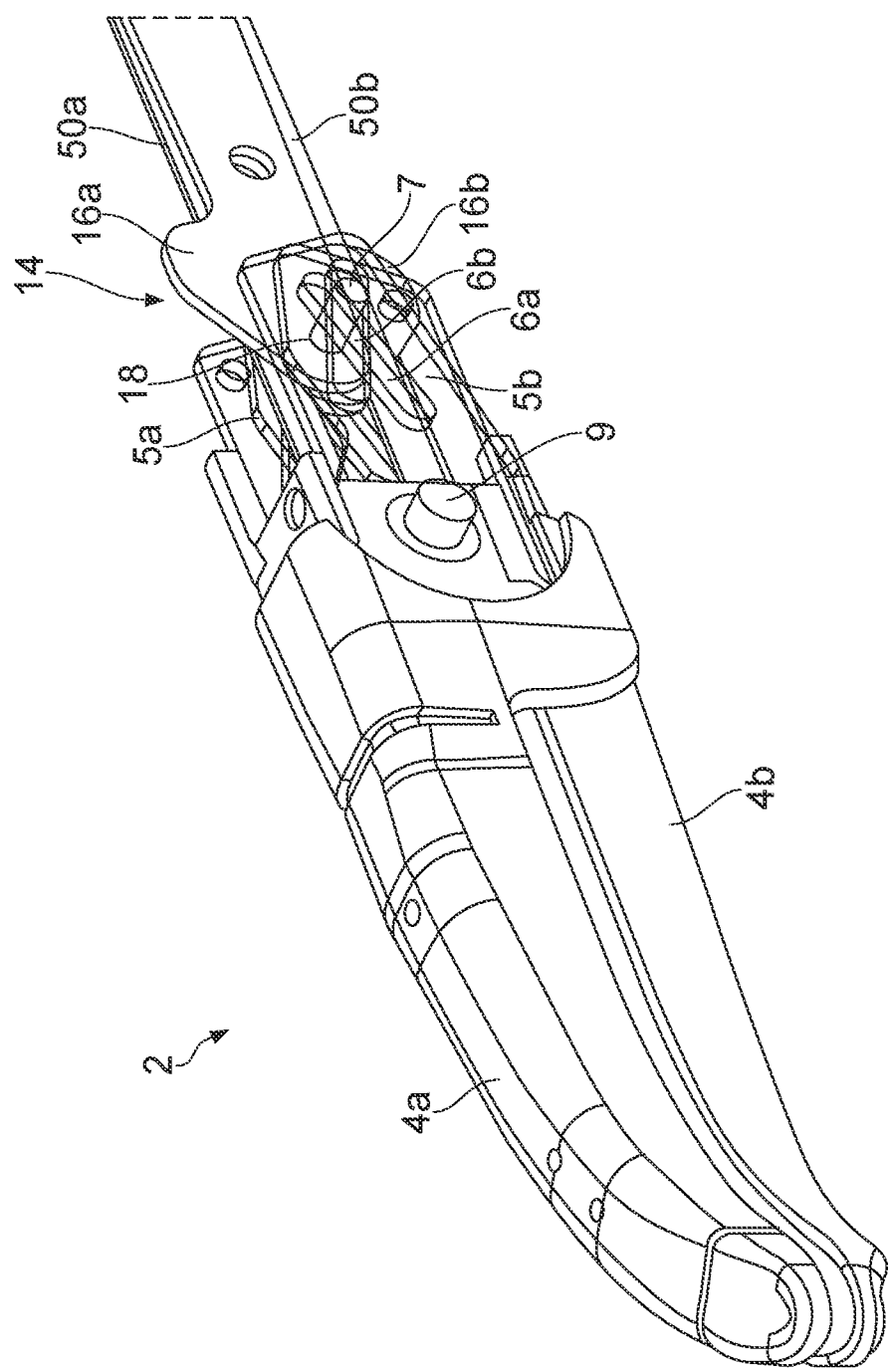
FIG. 7 further illustrates the drive assembly of the present invention connected to an end effector.

The distal end 14 of the drive shaft 12 is then coupled to a jaw assembly 2 configured as before. As shown in both FIGS. 6 and 7, the jaw assembly 2 comprises opposing jaw member 4a, 4b, pivotally connected by a pivot pin 9. The jaw members 4a, 4b each comprise a jaw flange 5a, 5b with a slot 6a, 6b. The drive shaft 12 is arranged so that the drive pin 7 extends through the two slots 6a, 6b and the drive hole 18 disposed on each flange 16a, 16b of the drive members 12a, 12b. Once assembled, the drive pin 7 will restrict any lateral movement of the drive members 12a, 12b relative to each other, and hold them in a fixed configuration. A proximal and distal movement of the drive pin 7 along the slots 6a, 6b by the drive shaft 12 thus causes one or both members 4a, 4b to move relative to the other such that the jaw members 4a, 4b move between an open position and a second position.

As the drive shaft 12 comprises two separate drive members 12a, 12b, a cutting blade assembly (not shown) may also be positioned in the space between the two drive members 12a, 12b and translated therealong. In use, once the jaw members 4a, 4b are in the closed position so as to grasp a portion of tissue, the blade may be translated in a proximal direction between the jaw members 4a, 4b so as to cut the tissue clasped therebetween. To enable this movement, the cutting blade assembly may comprise a cutting blade with a large longitudinal slot that also receives the drive pin 7, the slot being long enough that the movement of the drive pin 7 by the drive shaft 12 does not actuate the cutting blade, and conversely, the cutting blade can be actuated without being blocked by the drive pin 7.

As a result of this spade-like configuration of the drive shaft 12, the drive shaft 12 does not extend further into the jaw assembly 2, and therefore does not take up unnecessary space. Consequently, there is additional space in the jaw assembly 2 for cutting blade management. In this respect, the additional space provided by the drive shaft 12 of the present invention provides greater design freedom when manufacturing the jaw assembly 2, for example, the freedom to add features to the jaw assembly 2 that will help to guide the cutting blade and align the two jaw members 4a, 4b during actuation.

Furthermore, the two spade-like flanges 16a, 16b are configured such that their dimensions fit within the outer shaft 40 with minimal clearance to prevent the jaw members 4a, 4b from tilting when opening and closing. That is to say, the diameter of the flanges 16a, 16b substantially match the diameter of the outer shaft 40, such that they are able to move longitudinally along the outer shaft 40 to drive the drive pin 7 and actuate the jaw assembly 2, whilst minimising any lateral movement of the drive shaft 12 that would in turn move the drive pin 7 and jaw flanges 5a, 5b and thus cause the jaw members 4a, 4b to tilt.

Additionally, this arrangement provides additional space within the outer shaft 40 that allows connection wires 50a, 50b for connecting electrodes within the jaw members 4a, 4b to a power supply to be easily threaded around the outside of the two drive members 12a, 12b. In this respect, a first connection wire 50a can be positioned over the top of the second drive member 12b, and a second connection wire 50b can be positioned below the first drive member 12a. As each drive member 12a, 12b has a single spade-like flange 16a, 16b, this provides space for the connection wires 50a, 50b to run along the opposing side of the respective drive member 12a, 12b.

Figure 9:
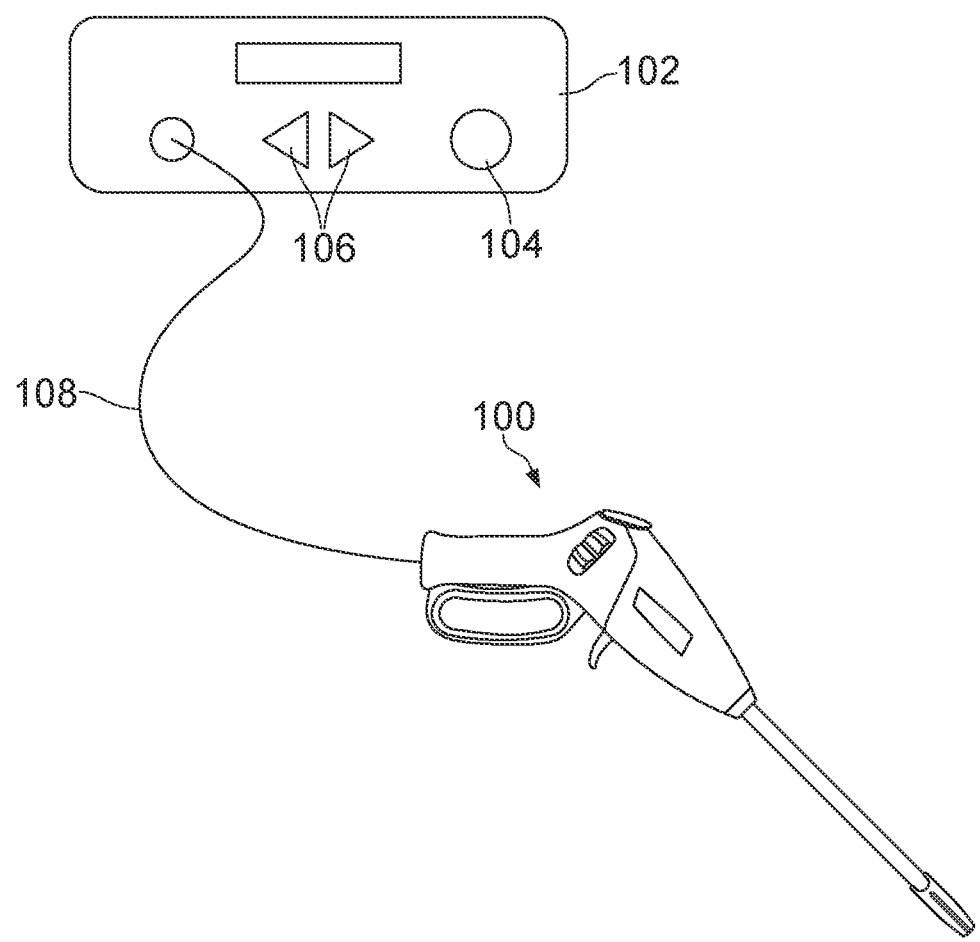
FIG. 9 illustrates a surgical system including an instrument having an end effector according to the present invention.

Referring now to FIG. 9, the drive shaft assembly described herein may be used as part of an instrument 100, which may in use be intended for connection to an electrosurgical generator 102 having a controllable radiofrequency (RF) source therein (not shown) that in use produces an RF coagulation signal that coagulates or seals tissue when applied thereto via electrodes located within the end effector of the instrument 100. Electrosurgical generator 102 includes control input switches 102 and 104, to respectively allow the generator to be turned on and off, and to allow the power of the RF coagulation signal fed to the instrument 100 to be controlled. In these respects, the electrosurgical generator 102 is conventional.

The instrument 100 may be connected in use to the generator 102 by a control and power line 106, which contains separate electrical lines to allow an RF signal to be fed to the end effector of the instrument 100 via internal wiring, and also to allow a control signal to be received from a switch (not shown) on the instrument 100, to command the electrosurgical generator 102 to output an RF coagulation signal to the instrument 100. In use, the surgeon activates the generator via on-off switch 104, and selects the coagulation or sealing signal strength to be generated by the internal RF source using buttons 102. During a surgical procedure with the instrument 100 when a sealing or coagulation RF signal is required at the end effector, the surgeon controls the generator 102 to produce such a signal by pressing the switch on the instrument 100, the generated RF signal then being passed via the electrical lines 106 to the end effector. That is, pressing of the switch in use causes an RF coagulation or sealing signal to be supplied to the appropriate electrodes contained within the end effector.

Various further modifications to the above described embodiments, whether by way of addition, deletion or substitution, will be apparent to the skilled person to provide additional embodiments, any and all of which are intended to be encompassed by the appended claims.

For example, in the above examples, the flanges 16a, 16b of the drive shaft 12 have a spade-like configuration, however, it will be appreciated that they may have any suitable configuration for restricting the lateral movement of the drive shaft 12, for example, a square, rectangular or circular configuration. Additionally, it is preferable that each drive member 12a, 12b has a single flange 16a, 16b, each extending in opposite directions perpendicular to the longitudinal axis of the drive shaft 12, in order to improve the ease of assembly and provide additional space for connection wires and the like. However, it was also be appreciated that the drive members 12a, 12b may each have two flanges extending in both directions perpendicular to the longitudinal axis of the drive shaft 12 and that such an arrangement will have the benefit of preventing the jaw members 4a, 4b from tilting.

The invention claimed is:

1. A drive shaft for a surgical instrument, comprising:
   a pair of opposing first and second elongate drive members configured to extend between an end effector and a handle of the surgical instrument, a distal end of the first and second elongate drive members being configured to actuate the end effector, and the first elongate drive member having a first proximal end and the second elongate drive member having a second proximal end, the first proximal end and the second proximal end being configured to be received within the handle, wherein:
   the first elongate drive member comprises at least a first flange extending from its distal end in a first direction perpendicular to a longitudinal axis of the drive shaft;
   the second elongate drive member comprises at least a second flange extending from its distal end in a second direction perpendicular to the longitudinal axis of the drive shaft; and
   wherein each of the first flange and the second flange is configured to receive a retention means,
   wherein the drive shaft is configured such that, in the absence of the retention means and upon exertion of a force on the respective flange, the distal end of the first elongate drive member and the distal end of the second elongate drive member are movable in a lateral direction relative to each other to permit the distal end of the drive shaft to pass through a retention molding for anchoring a proximal end of the drive shaft within the handle of the surgical instrument, and
   wherein in the presence of the retention means, the first flange and the second flange are held in a fixed configuration.

2. A drive shaft according to claim 1, wherein the first and second directions are opposing directions.

3. A drive shaft according to claim 1, wherein the first and second elongate drive members are connected at a first position towards the proximal end of the drive shaft.

4. A drive shaft according to claim 1, wherein the retention means comprises a drive pin, the drive pin being further configured to actuate the end effector.

5. A drive shaft according to claim 1, wherein the first and second flanges are configured such that the distal end of the drive shaft has a spade-like configuration.

6. An end effector for a surgical instrument, comprising:
   a pair of opposing first and second jaw members, the first and second jaw members being pivotally connected, each of the jaw members comprising a jaw flange extending from its proximal end, each flange having an elongate slot; and
   a drive assembly configured to move the first jaw member relative to the second jaw member from a first open position to a second closed position, the drive assembly comprising:
   a drive pin configured to be received by the elongate slots of the first and second jaw members, the drive pin being moveable between proximal and distal ends of the elongate slots; and
   a drive shaft according to claim 1, wherein the first flange of the first elongate drive member and the second flange of the second elongate drive member are configured to receive the drive pin as the retention means, the drive shaft being configured to move in a first direction along its longitudinal axis so as to actuate the drive pin longitudinally towards a distal end of the elongate slots to thereby move the first jaw member to the first open position, and further configured to move in a second direction along its longitudinal axis so as to actuate the drive pin longitudinally towards a proximal end of the elongate slots.

7. An end effector according to claim 6, further comprising an outer shaft extending from the first and second jaw members, wherein the drive assembly is located within the outer shaft.

8. An end effector according to claim 7, wherein the first and second flanges of the first and second drive members are configured such that lateral movement within the outer shaft is restricted.

9. An end effector according to claim 7, wherein a diameter of the distal end of the drive shaft substantially matches an internal diameter of the outer shaft.

10. An end effector according to claim 6, further comprising one or more electrical wires for connecting the first and second jaw members to a power supply, wherein the one or more electrical wires are arranged to run alongside one or both of the first and second elongate drive members such that the one or more electrical wires are positioned away from the first flange of the first elongate drive member and/or the second flange of the second elongate drive member.

11. An end effector according to claim 6, further comprising a blade assembly, the blade assembly having a cutting blade located at its distal end, wherein the cutting blade assembly is arranged to be moved in a longitudinal direction between the first and second elongate drive members such that the cutting blade is translated between the first and second jaw members.

12. A drive shaft according to claim 1, wherein the distal end of the first elongate drive member and the distal end of the second elongate drive member are squeezed together when being installed into the retention molding such that a diameter of the distal end of the first elongate drive member and the distal end of the second elongate drive member is reduced relative to a diameter of the distal end of the first elongate drive member and the distal end of the second elongate drive member before installation.

13. A drive shaft according to claim 1, wherein the distal end of the first elongate drive member is configured to move in a lateral direction to permit a temporary reduction of a width of the drive shaft.

14. A surgical instrument, comprising:
an end effector, the end effector comprising:
a pair of opposing first and second jaw members, the first and second jaw members being pivotally connected, each of the jaw members comprising a jaw flange extending from its proximal end, each flange having an elongate slot; and
a drive assembly configured to move the first jaw member relative to the second jaw member from a first open position to a second closed position, the drive assembly comprising:
a drive pin configured to be received by the elongate slots of the first and second jaw members, the drive pin being moveable between proximal and distal ends of the elongate slots; and
a drive shaft according to claim 1, wherein the first flange of the first elongate drive member and the second flange of the second elongate drive member are further configured to receive the drive pin as the retention means, the drive shaft being configured to move in a first direction along its longitudinal axis so as to actuate the drive pin longitudinally towards a distal end of the elongate slots to thereby move the first jaw member to the first open position, and further configured to move in a second direction along its longitudinal axis so as to actuate the drive pin longitudinally towards a proximal end of the elongate slots.

\* \* \* \* \*